United States Patent [19]

Russo

[11] 4,114,607
[45] Sep. 19, 1978

[54] INHALATION DEVICE

[75] Inventor: Ronald D. Russo, Hamden, Conn.

[73] Assignee: Chesebrough-Pond's Inc., Greenwich, Conn.

[21] Appl. No.: 753,839

[22] Filed: Dec. 23, 1976

Related U.S. Application Data

[63] Continuation-in-part of Ser. No. 657,242, Feb. 11, 1976, Pat. No. 4,060,074.

[51] Int. Cl.$^2$ .............................................. A61M 16/00
[52] U.S. Cl. ...................................... 128/2.08; 272/99
[58] Field of Search ..................... 128/2.08, 208, 147, 128/201, 145.8, 145.6, 2.05 V, 142 R, 185, 202, 205 R; 73/209 R, 419; 272/99 R; 46/44; 116/117 B, 117 C, 117 R

[56] References Cited

U.S. PATENT DOCUMENTS

| 393,869 | 12/1888 | Warren | 128/201 |
|---|---|---|---|
| 481,965 | 9/1892 | Orvis | 128/2.08 |
| 515,637 | 2/1894 | Wilhide | 272/99 R |
| 793,177 | 6/1905 | Cady | 128/208 |
| 892,432 | 7/1908 | Judson | 272/27 |
| 1,621,354 | 3/1927 | Dawley | 73/205 R |
| 1,926,748 | 9/1933 | MacKenzie et al. | 128/2.08 |
| 2,100,898 | 11/1937 | Bernett | 273/95 |
| 3,087,278 | 4/1963 | Waggle, Jr. | 46/44 |
| 3,633,421 | 1/1972 | Phillips | 73/209 |
| 3,635,214 | 1/1972 | Rand et al. | 128/2.08 |
| 3,695,608 | 10/1972 | Hanson | 128/2.08 |
| 3,754,546 | 8/1973 | Cooper | 272/99 R |

FOREIGN PATENT DOCUMENTS

| 1,112,252 | 8/1961 | Fed. Rep. of Germany | 128/272 |
|---|---|---|---|
| 8,662 of | 1903 | United Kingdom | 272/99 R |

Primary Examiner—Henry J. Recla
Attorney, Agent, or Firm—Morgan, Finnegan, Pine, Foley & Lee

[57] ABSTRACT

An incentive inhalation device which induces respiratory exercise and which is inexpensive, safe and easy to handle and operate. The device includes a container having a plurality of flow measurement chambers which are vertical when the device is in its upright position. In each chamber is housed a flow rate indicator, such as a light-weight article and ball, that normally rests at the bottom thereof. The bottom of each chamber is open to surrounding atmosphere and the top of each chamber is open to a passageway. In operation, the patient or user withdraws air from the air passageway and chambers. When the patient achieves the precalibrated flow rate or rates, the indicators will sequentially rise to the top of each chamber. In one embodiment of the invention the emphasis of the device is on duration by making the precalibrated rate of flow essentially the same for each chamber. In another embodiment of the invention the emphasis of the device is on increased effort and duration by having different precalibrated rates of flow for at least two of the chambers. To prevent disruption of air flow into the passageway and surprise or shock to the user, means are provided in the last chamber of the device to prevent the indicator from closing that chamber to the air passageway.

15 Claims, 15 Drawing Figures

INHALATION DEVICE

This application is a continuation-in-part of my application Ser. No. 657,242, filed Feb. 11, 1976 now U.S. Pat. No. 4,060,074.

FIELD OF THE INVENTION

The present invention relates to an incentive inhalation device which induces expansion and use of lungs and respiratory musculature.

BACKGROUND OF THE INVENTION

It is often necessary to induce patients to expand and use their lungs and respiratory musculature. Post-surgical, bedridden, inactive, obese and geriatric patients do not utilize their respiratory systems fully. Pain, illness and feebleness inhibit use. As a consequence, these people are prone to pulmonary complications such as lung congestion, atelectasis and pneumonia. The inefficient use of the respiratory system also can retard healing and cause muscle atrophy.

Thus, a need exists to provide patients with an incentive which encourages use of their respiratory systems. In general, presently available apparatus for inducing said use by inhalation is relatively expensive and awkward to handle. Further, the apparatus is comparatively costly and complex, and is generally limited to hospital use because of the complexities and costs. In addition, presently available apparatus is made up of a multiplicity of parts which, when dropped, are susceptible to breakage and which are costly to replace.

It is an object of this invention, therefore, to provide a new and improved device which induces progressive respiratory exercises through inhalation without drawbacks of presently available devices and systems.

Among the other objects of this invention is to provide an inhalation device which is safe to use; to provide an inhalation device, the successful use of which easily can be seen and measured by the patient, nurse or others; to provide an inhalation device which provides a progressive incentive and encourages use by ease of handling and operation; and to provide an inhalation device which accomplishes the foregoing while being relatively inexpensive.

Additional objects and advantages will be set forth in part hereinafter and in part will be obvious herefrom or may be learned with the practice of the invention, the same being realized and obtained by means of the respiratory stimulator recited in the appended claims.

SUMMARY OF THE INVENTION

In accordance with the invention, there is provided an inhalation device comprising a see-through container having a plurality of flow measurement chambers. In each chamber is a flow rate indicator, such as a lightweight article or ball, which normally rests at the bottom or lower portion thereof. A clearance fit is provided between each indicator and its chamber wall which allows for free vertical movement of the indicator but restricts air flow about the indicator, causing it to rise when a precalibrated inhalation effort is achieved. Extending into the lower portion of each chamber is an opening which connects the chamber to the surrounding atmosphere at a point where incoming air can lift the indicator when the user achieves the precalibrated rate of flow for that chamber. In the preferred embodiment the chambers are vertical and in adjacent compartments, and the lower openings are ports or slots which extend through the front and back walls thereof at a point at least partially below the flow rate indicators.

At the top portion of each compartment is an opening or port which connects the chamber to an air inhalation passageway. The passageway includes an outlet to which is connected means, such as a flexible tubing and mouthpiece, which allows a person to withdraw air from each chamber.

In a preferred embodiment the outlet is at the bottom and front of the device, and the passageway extends to the top of each compartment and in back of or along one side of the container so that the user and others easily can see each article or ball.

In use, a person places his or her mouth over the mouthpiece and inhales. This casues air to flow through the lower openings into the bottom of the chambers, up, against and around the indicators, through the chambers and the top ports into the air passageway. When a precalibrated inhalation effort is achieved by the user, the upward air flow in the chambers causes the indicators to sequentially rise to the top of the chamber. To prevent disruption of air flow into the passageway and surprise or shock the user, means are provided in the last chamber which prevent the indicator from closing the last top port.

The multi-chambered device of the invention is particularly useful for inducing progressive inspiration which meet desired inhalation efforts. The user readily can see progress, because with increased use of the lungs the user finds that he or she can raise a multiplicity of indicators. This device then provides incentive levels of achievement visible to the patient which are designed to correspond to increased use of the respiratory system and to progressive restoration and maintenance of lung capacity and musculatory strength.

With the multi-chambered device of the invention, the incentive levels can be provided in different ways.

In one embodiment this is achieved by causing the patient to inhale at a rate which at least corresponds to a precalibrated rate for a duration of time. For example, a precalibrated amount of inhalation for a predetermined time is required to raise the indicator to the top of the chamber closest to the passageway outlet and precalibrated additional amounts of inhalation for predetermined additional times are required to sequentially raise the indicator in the other chambers. In the embodiment illustrated in the drawings and disclosed hereinafter, at least 1000 cubic centimeters per second must be inspired by the user to raise the ball to the top of each chamber. Accordingly, when the desired flow rate is maintained for three seconds, all three balls will be at the top of the chambers indicating that at least 3000 cubic centimeters of air has been inspired.

Further, the incentive levels for a given multi-chambered device can be modified.

In one embodiment this is done by tilting the device, e.g., rearwardly, so that the indicators can be raised to the top of the container more easily. Particularly ill or feeble patients thereby are provided with an incentive level they can achieve, and, in so doing, otain needed respiratory exercise. To be able to accurately measure the flow rate when the container is tilted, means, such as a platform, are provided which can maintain the container at the desired angle. For example, when the container is tilted rearwardly 65°, an inhalation rate of only 650 cubic centimeters per second must be maintained for three seconds to sequentially raise the balls to the tops of the chambers.

Here, as in the previously described multi-chambered embodiment, to cause the flow indicators to sequentially rise a precalibrated withdrawal rate for a duration of time is necessary. In the previous example, at least 1000 cubic centimeters per second for three seconds is required, and in the present example, at least the reduced 650 cubic centimeters per second for three seconds is required. In these examples, the common factor is a given rate of withdrawal which at least meets the precalibrated rate of withdrawal of air from the chambers for a prescribed duration.

With this invention, the incentive levels also can be achieved by varying the inhalation effort from chamber to chamber. In a preferred embodiment this is accomplished by varying the gap between the chamber walls and the balls. It has been found that within limits the smaller the gap, the easier it is to lift the ball because a greater lifting force is provided by the incoming air. In an example of this embodiment the breadth of the chambers is constant and the size of the balls is decreased from the first to the last chambers. With this embodiment, an inhalation rate of 600 cubic centimeters per second can be required to lift the ball to the top of the first chamber, 900 cubic centimeters per second for a second chamber and 1200 cubic centimeters per second for a third chamber. Patients are thereby provided with progressive incentive levels of achievement which correspond to their recovery.

This embodiment is different than the previous embodiment where the required withdrawal of air is at a precalibrated constant rate for a predetermined duration, e.g., 1000 cubic centimeters per second for three seconds will cause the flow indicators to sequentially rise. Here, withdrawal of air at a rate of 600 cubic centimeters per second for any length of time will only raise the flow indicator in the first chamber. A patient must increase his inhalation rate to 900 cubic centimeters per second before the second flow indicator will rise, and to 1200 cubic centimeters per second before the third indicator will rise.

In this multi-chambered embodiment then, the emphasis is on increased effort and duration, whereas as in the previously described multi-chambered embodiments greater emphasis is placed on duration only.

The inhalation devices of the present invention, therefore, provide incentive levels for inducing respiratory exercises for the very feeble or seriously ill as well as for those who are well on their way to recovery.

In addition, a dispenser, such as a nebulizer, can be placed at the outlet end of the single or multi-chambered devices of the invention for inhalation of medicine upon inhalation by the patient.

Moreover, the device can include a bracket means for releasably holding the mouthpiece when it is not in use. In this way the tubing and mouthpiece will not flop about.

In construction, the devices of the invention are compact and safe. Within the inhalation passageway of each device there preferably is provided a filter which prevents loose particles picked up in the air flow from exiting and being inhaled by the user. In addition, where the device is made of several plastic components, they are placed together and preferably are ultrasonically welded into a single integral unit. This obviates the need of deleterious materials, such as glue, which are known to give off residual vapors over a long period of time.

BRIEF DESCRIPTION OF THE DRAWINGS

The following is a detailed description together with accompanying drawings of a preferred embodiment of the invention. It is to be understood that the invention is capable of modification and variation apparent to those skilled in the art within the spirit and scope of the invention.

In the drawings.

Figure 1:
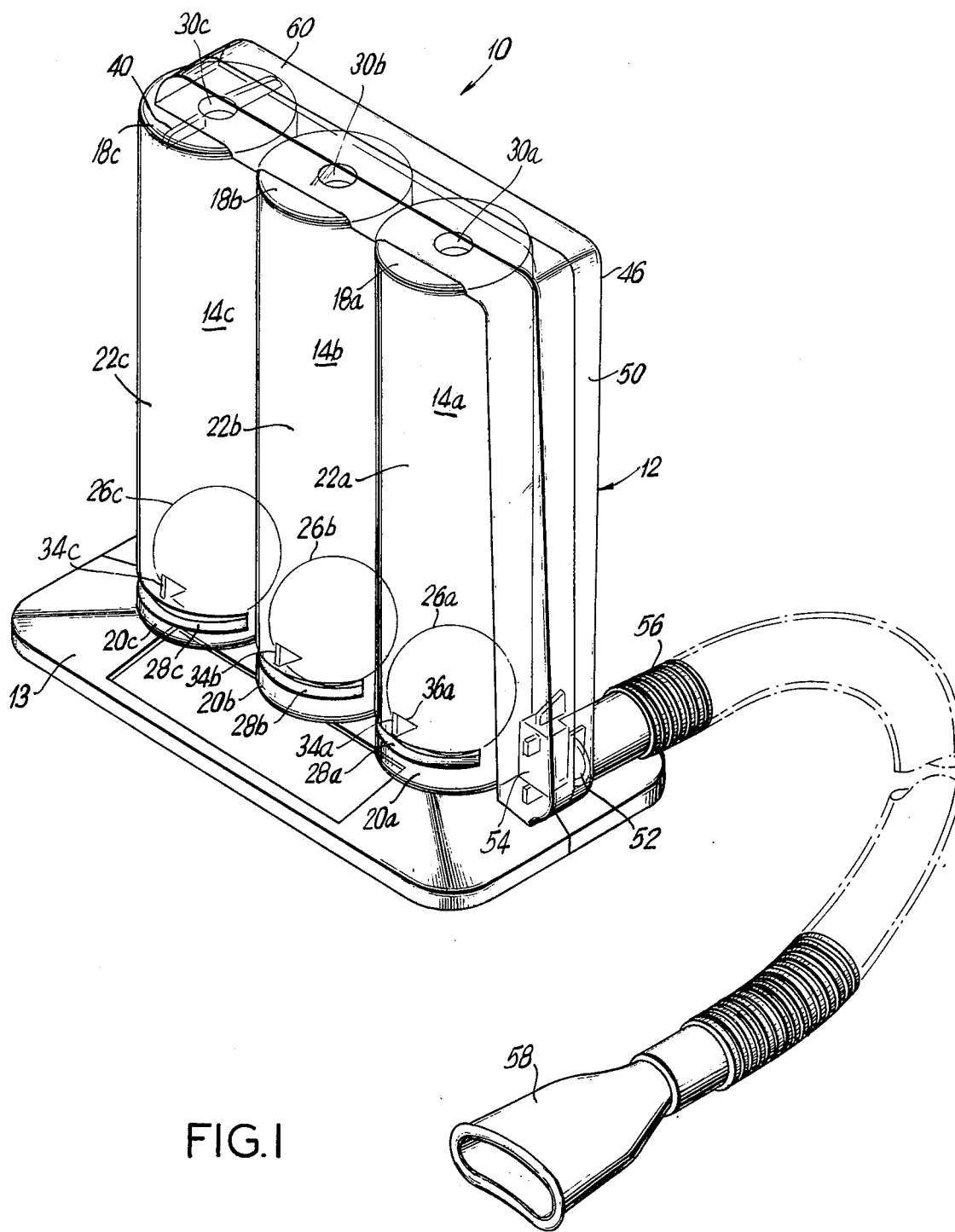
FIG. 1 is a perspective view of a multi-chambered inhalation device constructed in accordance with the present invention.

Referring first to the multi-chambered embodiment of the invention shown in FIGS. 1–7 of the drawings, the inspirator 10 is a transparent break resistant, integral unit which includes a container 12 mounted on a base 13. In the upright position the container 12 has three vertical compartments 14a, 14b, and 14c, spaced apart by the interconnecting webs 16a and 16b. The structure and function of the three compartments, 14a, 14b and 14c are identical. Accordingly, unless otherwise specified, the following description of compartments 14a applies equally to compartments 14b and 14c.

The compartment 14a has a top wall 18a, a bottom wall 20a and a transparent, vertical cylindrical wall 22a therebetween which form a vertical, flow measurement chamber 24a for a flow rate indicator, such as a plastic ball 26a.

The relative diameter of the ball 26a to the inner diameter of the cylindrical wall 22a is such that it provides for free movement of the ball 26a within the chamber 24a while providing a minimum clearance between the wall 22a and ball 26a. If the gap or clearance between the ball 26a and wall 22a is too small, the ball 26a may become stuck in the chamber 24a. If the gap is too large, the desired inhalation effort will not cause the ball 26a to rise. In an illustrative embodiment the total gap or clearance fit is about 0.40 inches between the balls 26a–26c and the inner surface of the walls 22a–22c. This is provided by having chambers 14a–14c with a diameter of about 1.040 inches and balls 26a–26c with a diameter of about 1.00 inches.

Extending through and across the front and back of the lower portion of the compartment wall 22a is a rectangularly shaped slot 28a which connects the lower portion of the chamber 24a to the surrounding atmosphere. Inasmuch as the compartment wall 22a is cylindrical, slot 28a also is in the shape of an arc. The dimensions for each segment of the slot 28a are 1.250 inches in length and 0.156 inches in height.

Extending through the center of the top wall 18a is a port 30a which connects the top portion of chamber 24a with an overhead passageway, hereinafter described in detail. The breadth of the port 30a allows for the withdrawal of air from the chamber 24a which causes the ball 26a to rise while being adapted to be closed by the ball 26a when it reaches the top of the chamer 24a when the user inspires air at the desired rate. In the illustrated embodiment the port 30a has a diameter of about 0.3125 inches.

To facilitate the rise of the ball 26a, opposing ridges 32a and 34a extend inwardly from the front and back portion of the cylindrical wall 22a immediately above the slot 28a. Each ridge 32a, 34a, is in the form of a right triangle with the hypotenuses thereof forming the upper and downwardly sloping surface 36a. The ball 26a normally rests on these downwardly sloping surfaces 36a so that only the lowermost segment of the ball 26a extends across the upper portion of the slot 28a.

To prevent a disruption of air flow by reason of the balls 26a, 26b and 26c, rising to the top of their chambers 24a, 24b and 24c, a ridge 40 is provided in the last chamber 24c which depends downwardly from the top wall 18 adjacent to the port 30c. In use, the ball 26c cannot close port 30c and interrupt the flow of air to cause surprise and shock to the user.

The supporting base 13 extends beyond the container 12 and enables the device 10 to stand by itself in a vertical upright position. As illustrated, the base 13 is rectangularly shaped and is in the form of an inverted curved disc-like structure. The container 12 is centrally positioned on the upper convex platform surface and the platform 13 itself stands on its outer perimeter.

About one side and top of the container 12 is an inverted "L" shaped channel 46 which forms an air inhalation passageway 48.

Figure 4:
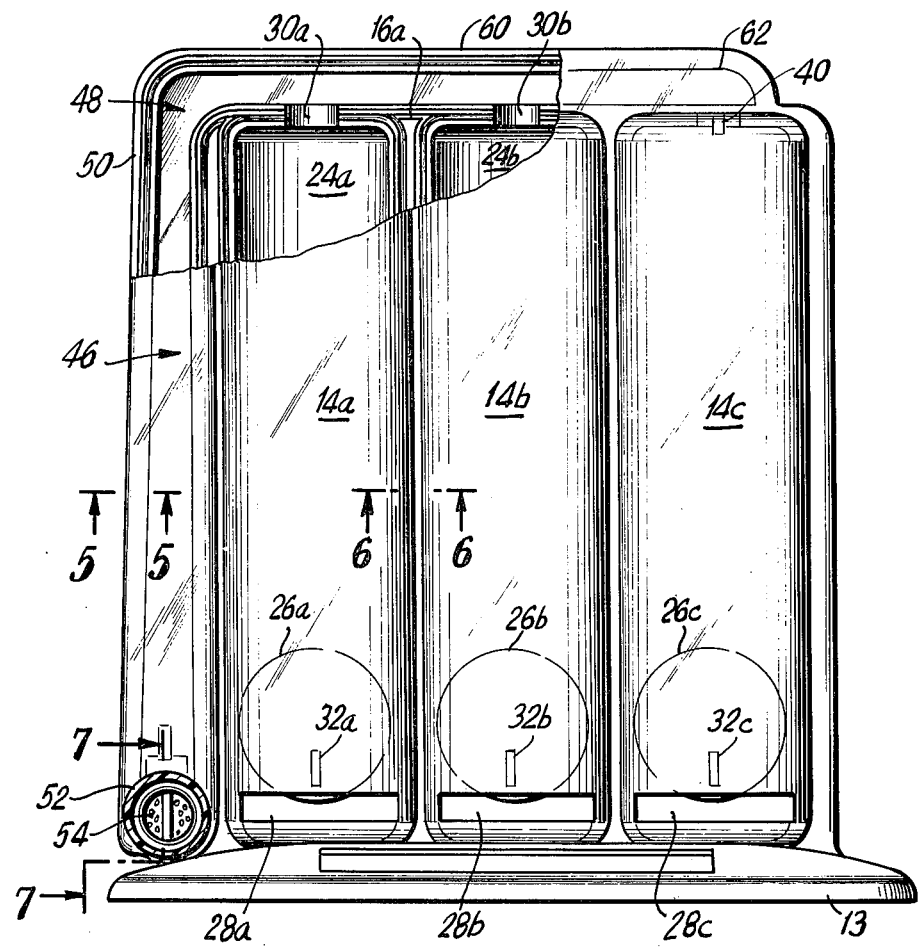
FIG. 4 is a front view of the device illustrated in FIG. 1.

As shown in FIG. 4 the horizontal section 60 of the passageway 48 extends over the central portion of the top walls 18a, 18b and 18c of the compartments 16a, 16b and 16c, opens to top ports 30a, 30b and 30c, and terminates in the closed outer end 62.

Figure 3:
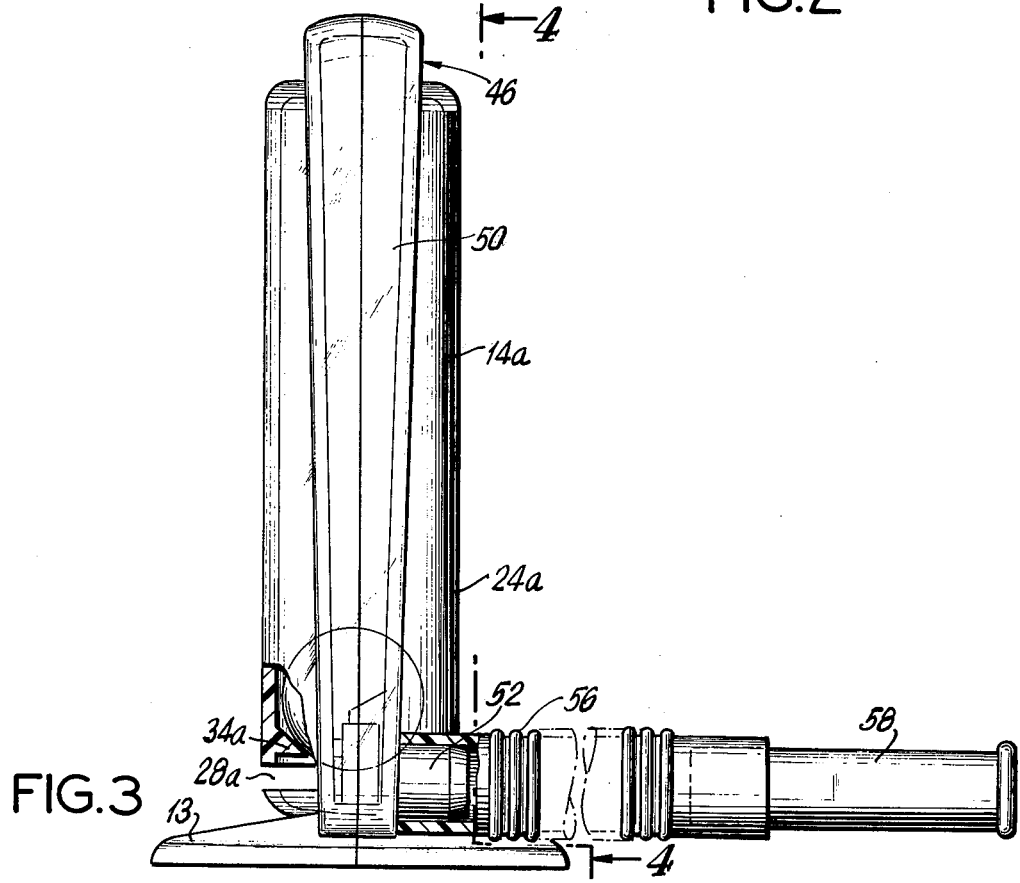
FIG. 3 is a side view of the device illustrated in FIG. 1 in which the bottom of the container is partially broken away to show details in construction.

As illustrated in FIG. 3 the vertical section 50 of the channel 46 is tapered with the narrowest segment at the bottom of the container 12 connected to a tubular outlet 52.

The outlet 52 extends horizontally and outwardly over the base 13. Forced fitted into the outlet 52 is a rectangularly shaped filter 54 which captures loose particles that may pass into the passageway upon inhalation.

In the illustrative embodiment the filter 54 is made from urethane foam of about 0.620 inches in length and 0.370 inches in height and 0.187 inches in thickness. The illustrated filter 54 has 10 pores per inch and presents a tortuous path for air flow so that loose particles are prevented from passing therethrough.

Slidably fitted over the outlet tube 52 is flexible accordian tubing 56 which has at its other end a mouthpiece 58 slidably fitted thereinto. Flexible tubing 56 of some 11.0 inches has been found desirable and convenient to use.

Further, the device of the invention is compact and easy to handle. The device of the illustrative embodiment stands some six inches high and is about six inches in length and is about three inches wide. Patients, therefore, can easily handle and operate the device.

In operation, the patient or user places his or her mouth over the mouthpiece 58 and inhales. This action causes air to be initially withdrawn from the air passageway 48 and chambers 24a, 24b and 24c. Because the first chamber 24a is closest to the point of inhalation, air flow through 28a into chamber 24a initially will be greater than in the other chambers 24b and 24c. Accordingly, inhalation at a precalibrated rate will cause the air flow into chamber 24a to first lift the ball 26a to the top of the chamber where it will close port 30a. Sustained inhalation at the precalibrated rate will cause the next ball 26b in the chamber 24b to rise and close port 30b. Finally, ball 26c in the last chamber 24c will rise to the top and come into contact with depending ridge 40 without abruptly disrupting air flow. The balls 26a, 26b and 26c will remain at the top of the chambers 24a, 24b and 24c as long as the user continues to expend a sufficient inhalation effort.

Throughout the action of the balls 26a, 26b and 26c is seen clearly because the air passageway 48 is alongside and on top of the container 12 giving the user an unimpeded view.

This device of the present invention therefore measures the minimum flow rate of inspiration needed to lift and maintain the balls 26a, 26b and 26c at the top of the container 12. In the illustrative embodiment of the device shown in the drawings, each ball 26i a, and 26b and 26c is about 1.0 inches in cross-section and weighs 1.5 grams, and each chamber 24a, 24b and 24c is about 4.70 inches in height and about 1.040 inches in cross-section. To raise the balls 26a, 26b and 26c in their respective chambers 24a, 24b and 24c, the user must inspire 1000 cubic centimeters per second of air. Thus, to raise the ball 26a the user must inspire still another 1000 cc per second. To sequentially raise all three balls to the tops of their chambers, the user must inspire at least 3000 centimeters in three seconds. For convenience the foregoing information may be imprinted directly on the base 13 or a label affixed to the base 13.

The flow rate of 1000 cubic centimeters per second used for the illustrative embodiment of the device of FIGS. 1-7 corresponds to a normal full deep breath. In accordance with this invention flow rates of the device 10 can be changed to correspond to the condition of the patient.

Figure 7:
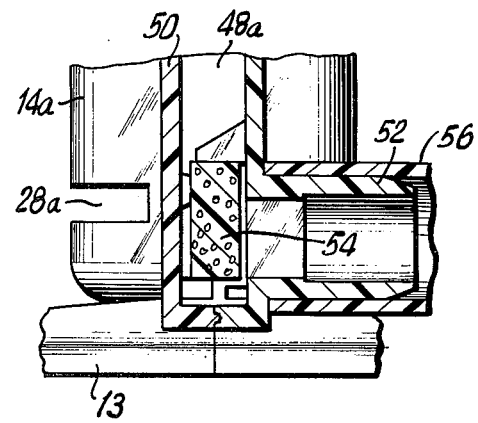
FIG. 7 is a sectional view of FIG. 4, taken along lines 7—7, showing the filter in air passageway which prevents loose particles from being inhaled.
Figure 8:
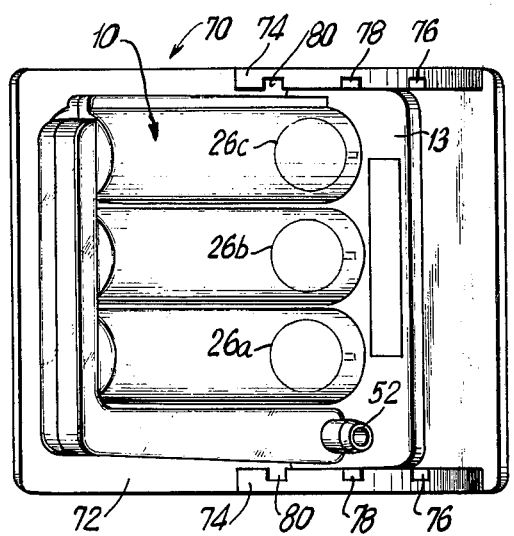
FIG. 8 is a plan view of the platform for maintaining the container at predetermined angles.
Figure 9:
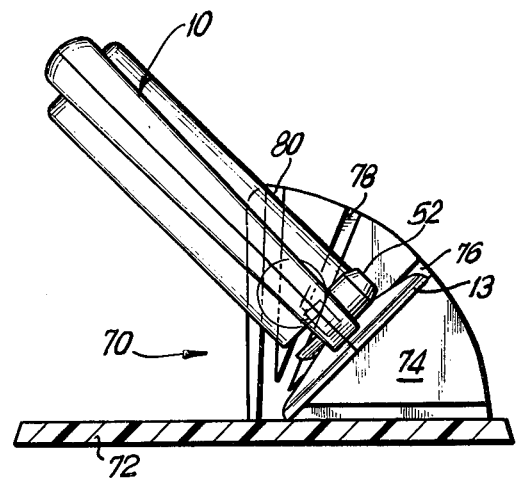
FIG. 9 is a side view of the platform with the foreground side wall removed to more clearly show the grooves into which the base of the device is slidable.

In one embodiment, the device 10 can be tilted to reduce the flow rate needed to raise and maintain each ball 26a, 26b and 26c at the top of the container 10. In the device 10 shown in the drawings by tilting the device 10 rearwardly, the lifting force needed to overcome the force of gravity is reduced. The greater the tilt the less the inhalation effort needed to achieve lifting and maintaining the ball at the top of the container 12. In tilting the device 10, however, it becomes more difficult to measure flow rate when the angle of tilt cannot be ascertained. To overcome this difficulty, the present invention includes, as shown in FIGS. 7 and 8, a platform 70 having a self-standing base 72 and two side walls 74. Included in each side wall are grooves 76, 78 and 80 which are set at 45°, 65° and 85° to the base 72. In use, base 13 of the container 12 is slidable into opposing grooves so that any one readily can tell the angle of the tilt.

The device 10 illustrated in the drawings is precalibrated to provide a flow rate for each chamber of 750 cubic centimeters per second at 45°; 650 cubic centimeters per second for each chamber at 65°; and 250 cubic centimeters per second for each chamber at 85°.

Thus, regardless of the condition of the patient, the present invention provides an incentive for a patient to use his or her lungs and chest. As that patient recovers, the angle of the tilt can be reduced until the device is vertically upright. In this way, the patient realizes his or her improvement.

In these illustrative multi-chambered embodiments of the invention, the incentive levels are based upon an inhalation effort which must correspond to at least a precalibrated rate of withdrawal of air from the chambers for a predetermined duration of time. For instance, the example of the device shown in FIGS. 1-7 requires at least 1000 cubic centimeters per second for three seconds. With the platform this rate can be changed but the emphasis is still on meeting a precalibrated rate for duration of time.

It is also within the scope of this invention to vary the inhalation effort from chamber to chamber. With these embodiments of the invention greater emphasis is placed on increased effort rather than duration.

Figure 10:
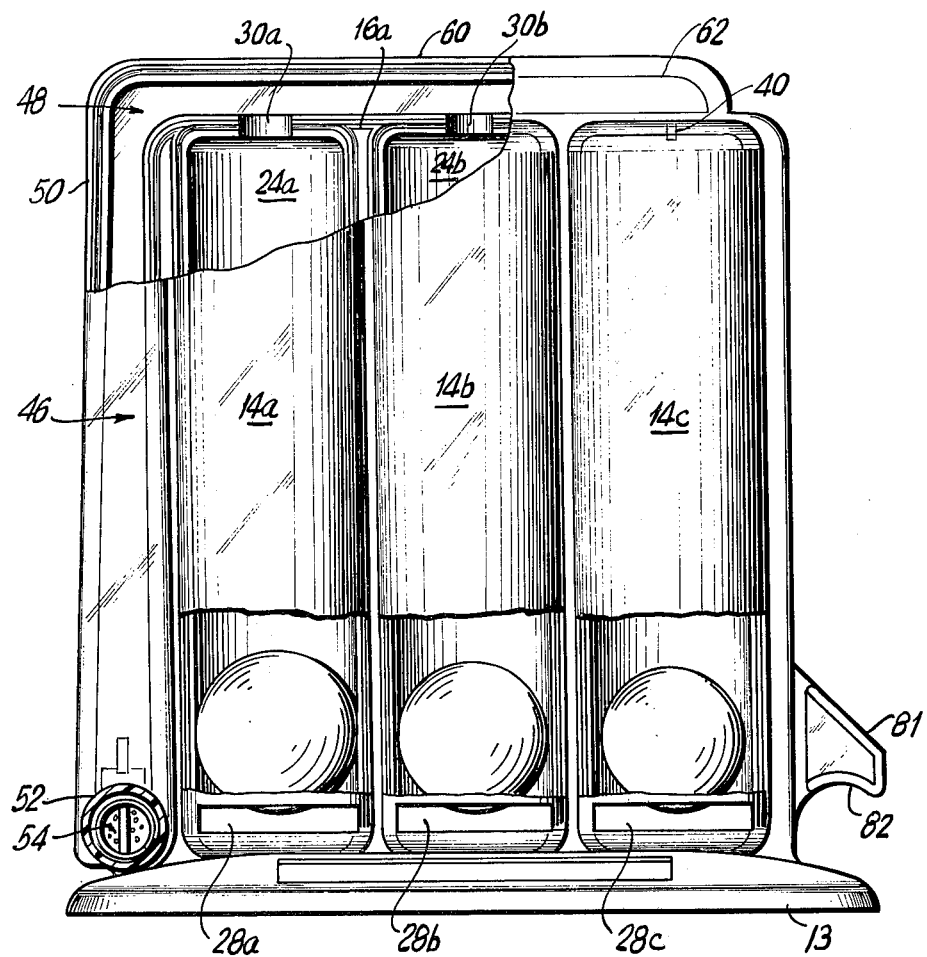
FIG. 10 is a side view of an embodiment of the mutli-chambered inhalation device of the invention in which the precalibrated rate of flow is varied from chamber to chamber by providing different size flow indicators in the chambers.

As shown in FIG. 10 this is accomplished by varying the gap between the compartment walls 22a-22c and flow indicators or balls 26a-26c in each chamber 14a-14c.

It has been found, for example, that, in general, by decreasing the gap between the flow indicators, such as the lightweight articles or balls 26a-26c, and the chamber walls 22a-22c, while maintaining a clearance fit for free vertical movement, it is easier to cause the balls 26a-26c to rise. This is due to the fact that more incoming air contacts and lifts the indicators 26a-26c. Conversely, it has been found that, in general, by increasing the gap between the balls 26a-26c and the chambers 22a-22c, it is more difficult to cause the balls 26a-26c to rise. In this instance the amount of air acting on the balls 26a-26c is decreased. At the same time the interaction between the chambers 14a-14c must be considered in arriving at the desired inhalation effort for each chamber.

For example, with a gap of about 0.25 inch between the ball 26a and wall 22a in the first chamber 14a, a gap of 0.050 inch in the second chamber 14b and a gap of 0.100 inch in the third chamber, a device is provided in which the balls in the chambers will rise at different flow rates; e.g., 600 cubic centimeters per second for the first chamber, 900 cubic centimeters per second for the second chamber and 1200 centimeters per second for the third chamber. In this preferred embodiment the changes in the gaps are achieved by changing the size of the balls 26i a-26c shown in FIGS. 1-7 without any other modification to the device. In an illustrative example of the embodiment of the invention shown in FIG. 10 the height of the chambers 14a-14c is about 4.70 inches and the inner diameter of the chambers 14a-14c remains about 1.040 inches, while the diameter of the ball 26a in the first chamber 14a is increased to 1.015 inches and the balls 26b and 26c are decreased to diameters of 0.990 inches and 0.940 inches, respectively. The weight of the balls 26a-26b are 1.5 grams and the weight of the ball is 26c is 1.7 grams.

This example also demonstrates the consideration which must be given to the interaction between chambers 14a-14c and indicators 26a-26c once changes are made. For chamber 14b, 1000 cubic centimeters per second are required to lift the ball 26b to the chamber 14b. This is the same withdrawal rate required to lift the ball 26b in the chamber 14b of the illustrative example for the device shown in FIGS. 1-7 . Yet, in the present example the size of the ball 26b has been reduced from 1.00 inches to 0.990 inches. In the present illustrative example this change had to be made because a larger ball 26a in the first chamber 14a causes less air to be withdrawn from the first chamber 14a before the air began to be withdrawn from the second chamber 14b. At the same time the diameter of the ball 26c was decreased, its weight was increased in order to achieve the desired rate of flow.

Further in this embodiment greater emphasis is placed upon increasing the inhalation effort of the patient from level to level rather than having the patient maintain a constant effort for a prescribed duration. For example, should a patient withdraw air at the rate of 600 cubic centimeters per second for 3 seconds, that patient only will cause the ball 26a in the first chamber 14a to rise. To cause the balls 26b and 26c in the second and third chambers to rise, the patient must increase his inhalation effort, e.g., to 900 cubic centimeters per second to raise the ball 26b in the second chamber and 1200 cubic centimeters per second to raise the ball 26c in the third chamber. This particular embodiment of the invention is useful where the patient may be especially feeble or ill. In utilization, patients readily can achieve the first level, and as they become stronger they can achieve the higher and more difficult levels. At each level, however, the patient benefits by being induced to perform respiratory exercises.

Figure 11:
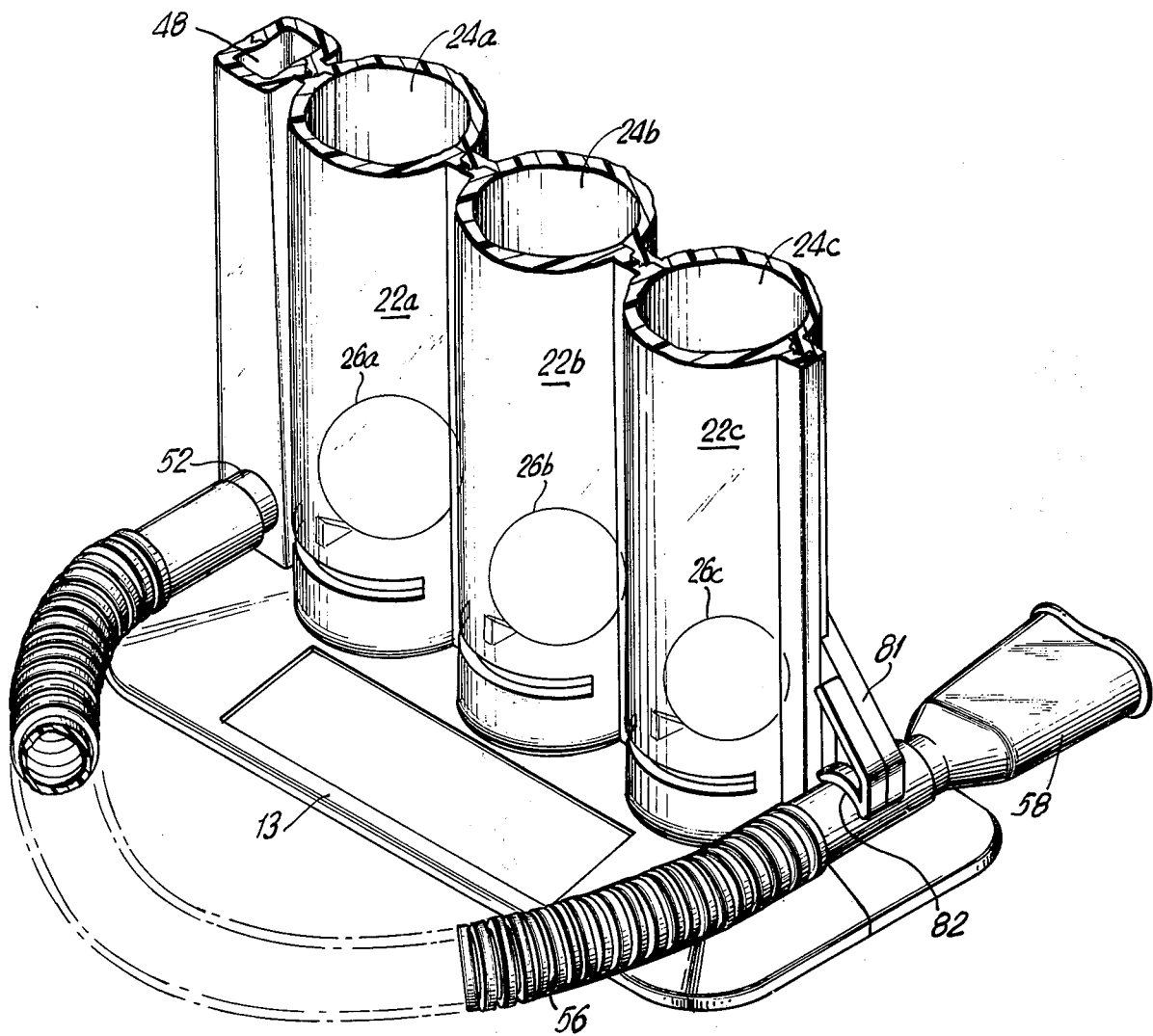
FIG. 11 is a perspective view of the lower portion of the device of FIG. 12 wherein a bracket or tab releasably holds the mouthpiece to the device when it is not in use.
Figure 12:
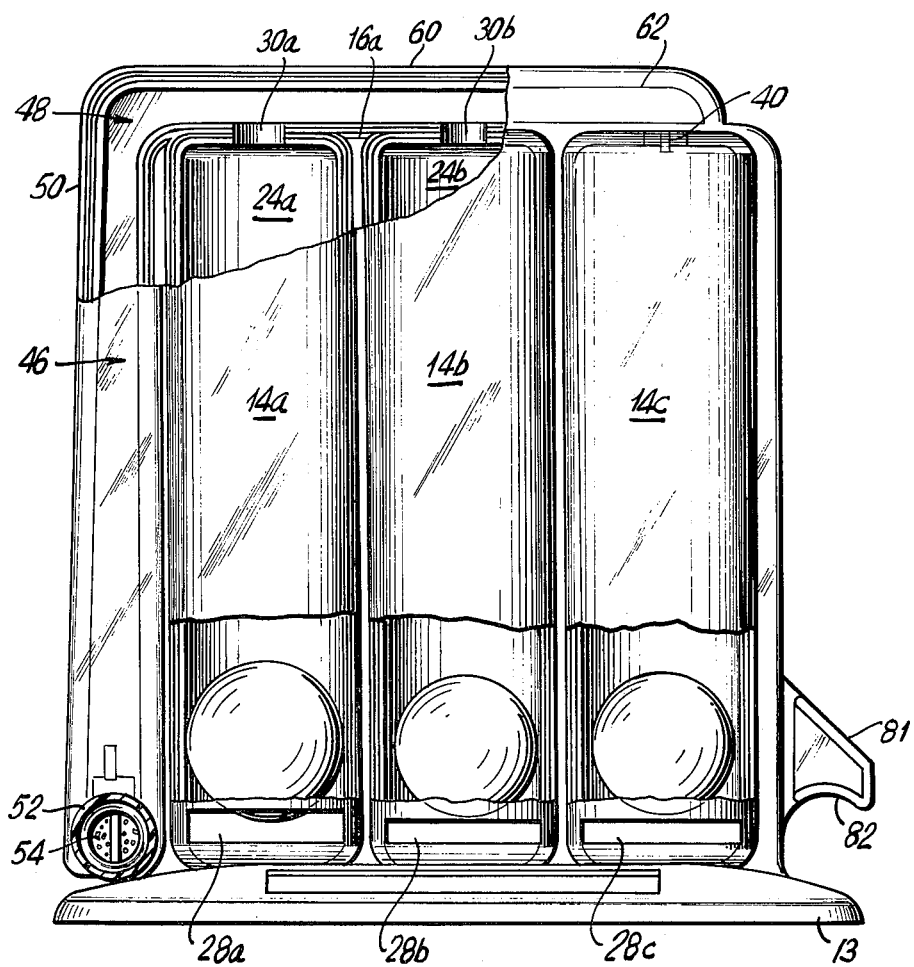
FIG. 12 is a side view of still another embodiment of the multl-chambered inhalation device of the invention in which the precalibrated rate of flow is varied from chamber to chamber by providing a ball of increased size in the first chamber and by decreasing the height of the slots extending across the bottom of remaining chambers.
Figure 13:
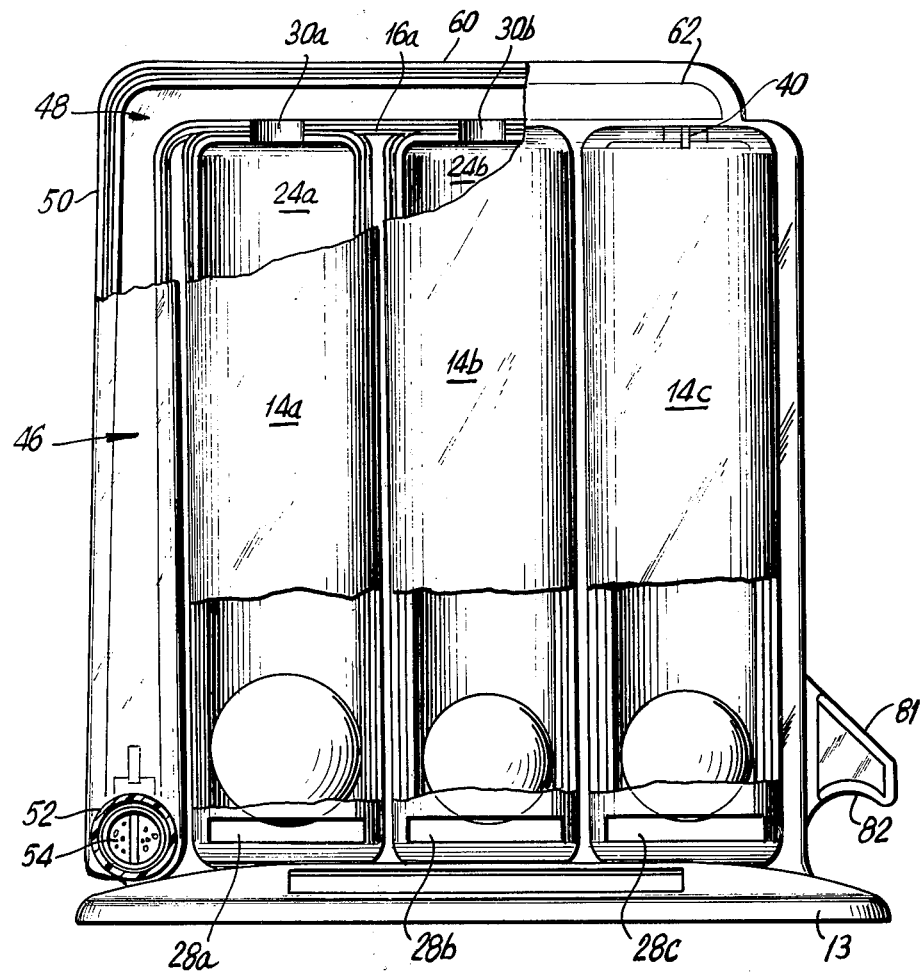
FIG. 13 is a side view of another embodiment of the multi-chambered inhalation device of the invention in which the precalibrated rate of flow is varied from chamber to chamber by providing a ball of increased size in the first chamber and by decreasing the breadth of the remaining chambers.

Other multi-chambered embodiments of the devices of the invention which change the incentive level are shown in FIGS. 11 and 12.

In FIG. 11 the size of the ball 26a in the first chamber 14a is changed and the dimensions of the slots 28b and 28c in the second and third chambers 14b and 14c are changed, otherwise the structure and dimensions of the parts shown in FIGS. 1-7 remain the same. With these changes a device is provided which requires different levels of inhalation effort for raising the balls 26a-26c in each of the chambers 14a, 14b or 14c.

Surprisingly, it has been found that increasing the slot size does not reduce the inhalation effort to raise the ball. It is believed that the determining factors in reducing the amount of effort required is the cross-sectional area of the gap between the ball and chamber wall. Accordingly, in FIGS. 10 and 11 a larger ball 26a in the first chamber 14a reduces the inhalation effort required to lift that ball, e.g., from 1000 cubic centimeters per second for a one inch ball to 600 cubic centimers per second for a 1.015 inches outside diameter ball.

In FIG. 12 the size of the ball 26a in the first chamber 14a again is increased to reduce the inhalation effort required to lift the ball 26a in that chamber, while the diameter of the chambers 14b and 14c is decreased to change the inhalation effort required to lift the balls 26b and 26c in those chambers. As in the other embodiments, the changes are made relative to another to compensate for the effect the changes in one chamber or ball will have upon the other chambers and balls.

In addition, incentive levels provided by the present invention can be achieved by using devices with different numbers of chambers 14. For example, a two chambered device of the invention can be used when respiratory exercises are initiated and a four chambered device substituted when the patient is well on the way to recovery. In each instance, moreover, the emphasis can be placed upon duration alone or upon increased levels of achievement with duration.

As illustrated in FIGS. 10–11, the devices of the invention also can include a tab or bracket 81 for releasably holding the mouthpiece 58 to the device. In this way the tubing 56 and mouthpiece 58 will not flop about when the device 10 is not in use. When the device 10 is to be used the mouthpiece 58 is simply pulled out from under the bracket 81.

As shown, the bracket 81 is integral with the end of the device 10 opposite the outlet end and is spaced above the platform 13. The bracket 81 is in the general shape of an outwardly and downwardly projecting curved finger forming a groove 82 between the bracket 81 and platform 13 for holding the reduced portion of the mouthpiece 58 which receives the flexible tubing 58.

In the embodiments illustrated in the drawings, the inspirators 10 preferably are formed in a two part conventional injection mold. Each part is a vertical section of the inspirator which, as illustrated in FIG. 2, is one-half of the assembled inspirator taken along the longitudinal or transverse center line.

Figure 2:
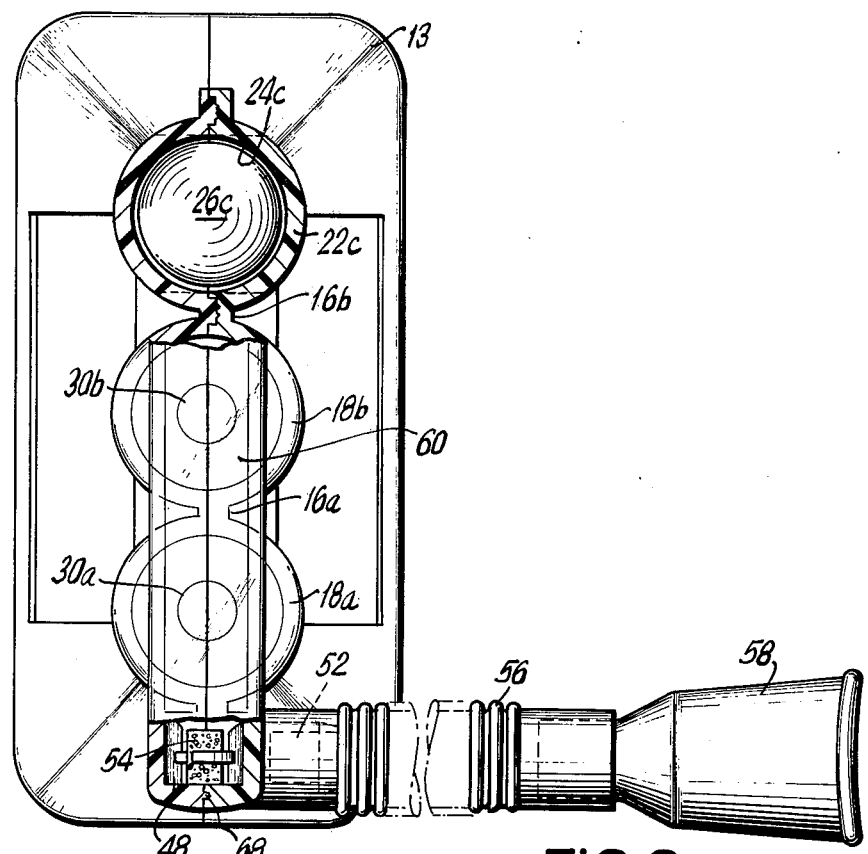
FIG. 2 is a plan view of the device illustrated in FIG. 1 with the top of the container broken away to show details in construction.
Figure 5:
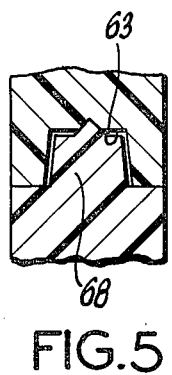
FIGS. 5 and 6 are sectional views of FIG. 4, taken along the lines 5—5 and 6—6, illustrating the tongue and groove construction of the mating parts of the device.
Figure 6:
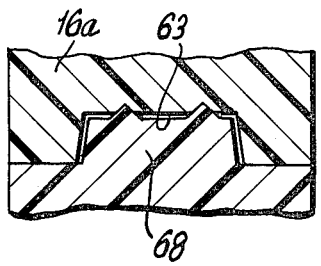

As illustrated in FIGS. 2, 5 and 6, the face of the rear sections of the multi-chambered devices are formed with tongues 68 in the outer channel and container walls and the intermediate interconnecting webs 16a and 16b. Correspondingly, the front section of the multi-chambered devices are formed with grooves 63 in the correspondingly front wall sections into which slidably fit the tongues 68.

In assembling the illustrated multi-chambered inspirators 10, the filter 54 is inserted in the outlet 52, balls 26a, 26b and 26c are placed in one section of the container 12 and the molded sections are brought together so as to cause the tongues 68 to fit into grooves 63. With the inspirators 10 so assembled, the sections are ultrasonically welded together to form single integral multi-chambered devices 10 of the invention.

In each embodiment ultrasonic welding is preferred because it obviates the need for glue which can produce long lasting deleterious vapors.

With respect to materials for forming the devices of the invention plastics are used which preferably are inert and stable in the formed device and which lend themselves to processing by plastic forming techniques, and will, when formed, provide the see-through, self-supporting device described and claimed herein. In the preferred embodiment the device is formed by injection molding polystyrene. Other materials and plastics which provide the described properties can also be used, including styrene-acrylonitrile copolymers, rigid polyvinylchloride polymers and polycarbonate polymers.

Figure 14:
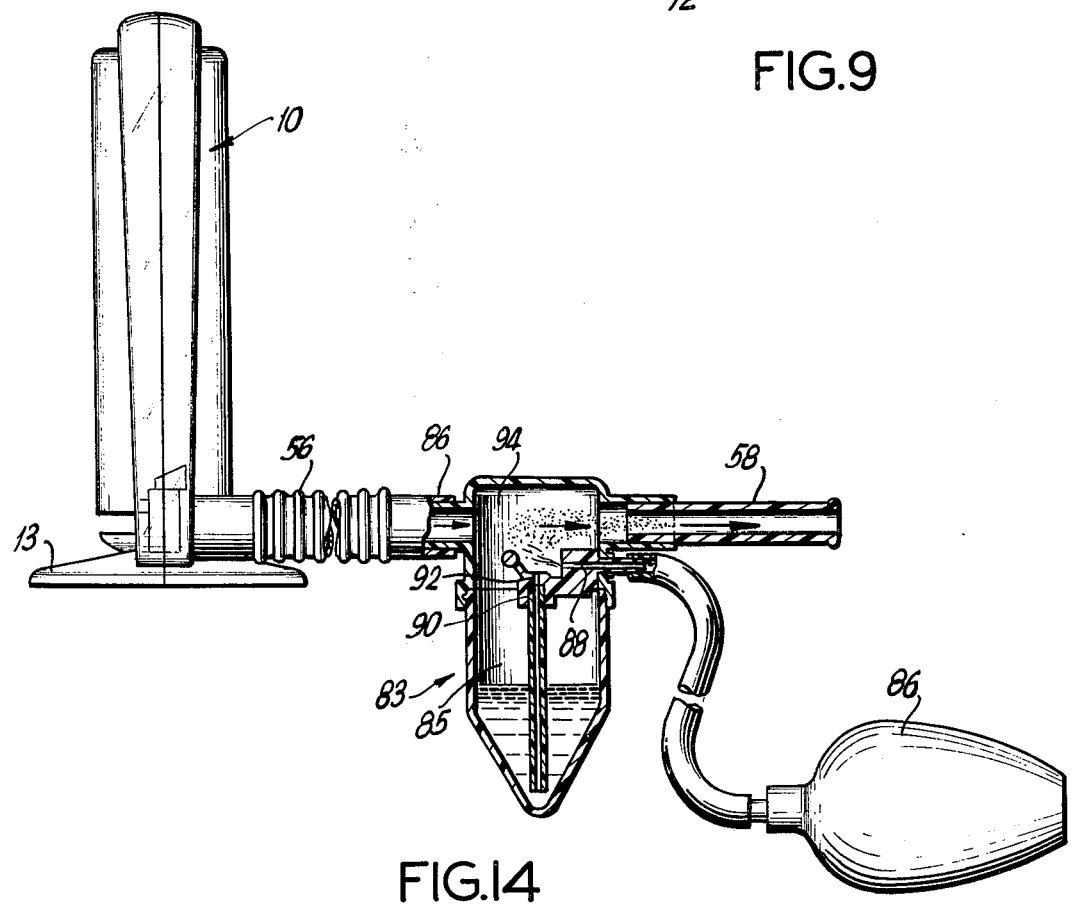
FIG. 14 is a side view, partially broken away, to show the dispenser for dispensing medicine through the flexible tubing upon inhalation.
Figure 15:
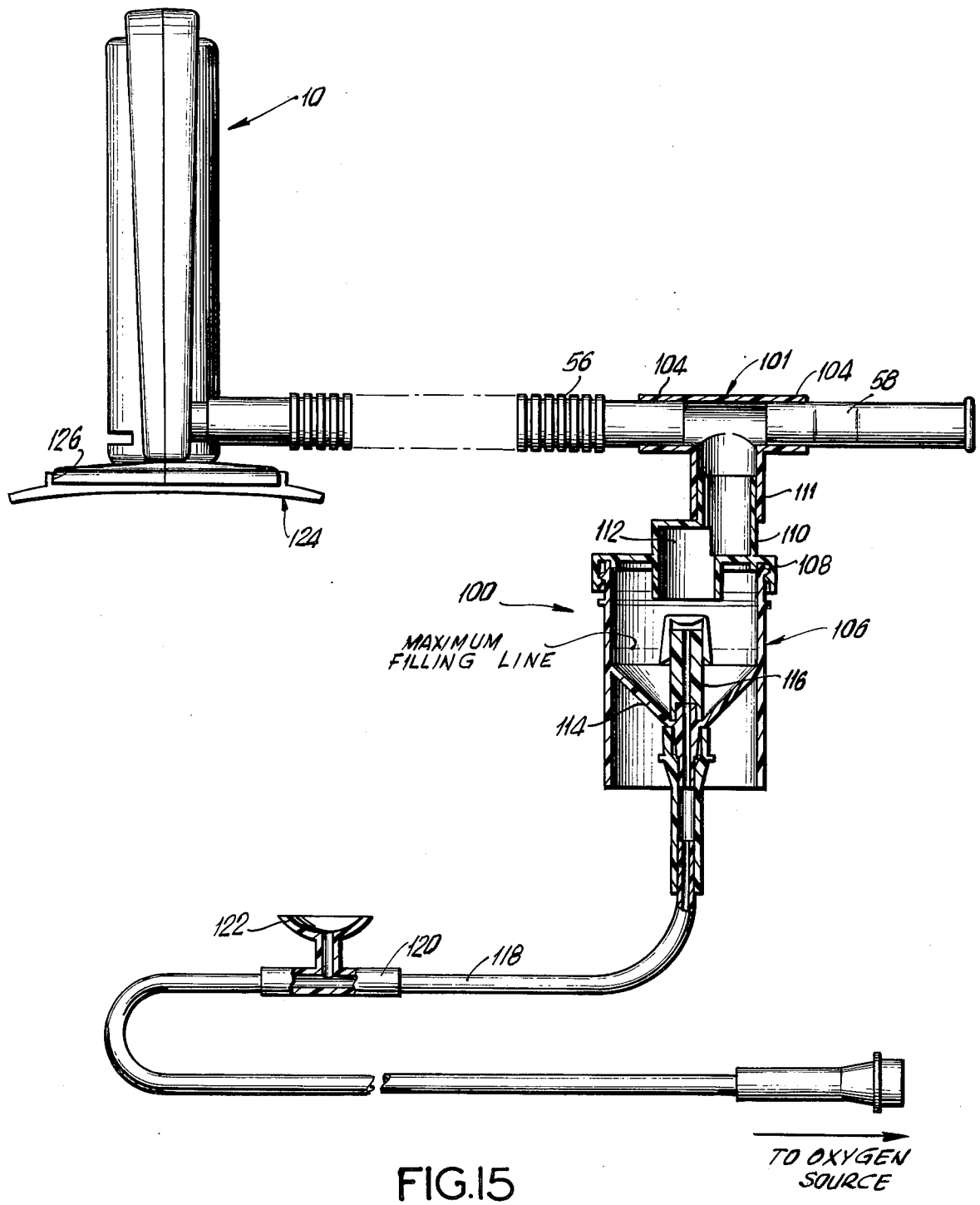
FIG. 15 is a side view, partially broken away, to show another dispenser for dispensing medicine through the flexible tubing upon inhalation.

As shown in FIGS. 14 and 15, the present invention can employ medicinal dispensers 83 and 100, respectively, connected to the device 10 between the tubing 56 and mouthpiece 58. Upon inhalation the patient will inspire the medicine in spray or powder form as he or she exercises his or her lungs and musculature. The illustrated medicinal dispensers 83 and 100 can be used to dispense bronchial dilators, water vapor, anti-inflammatory agents and asthmatic and other medicines.

In FIG. 14 the dispenser 83 is directly connected at one end 84 to the mouthpiece 58 and at the other end 86 to the flexible tubing 56. The reservoir 84 is filled with medication usually around 5cc. The patient inhales trying to raise the balls 26a, 26b and 26c. While inhaling, he squeezes on the bulb 86. Air from the bulb 86 is forced through the nozzle 88 and across the tip of the tube 90. This rapidly-forced air creates an upward venturi suction in the tube 90 thus lifting up medication from the reservoir 84. As medication squirts out the tube 90, the rapidly-forced air breaks up the liquid into an aerosol mist. The aerosol is further atomized by the diffuser 92 into smaller particles. Atomized medication is now in the upper mist chamber 94. Inhaled patient air rushes across the mist chamber thus carrying the atomized medication into the respiratory system of the patient. Large, unwanted particles fall back down into the reservoir. Only the desired small 0.5 micron to 6 micron particles are inhaled to reach deep into the lungs. The amount of medication delivered is controlled by viewing through the reservoir.

In FIG. 15 a hollow T-shaped manifold 102 is used to connect the medicinal dispenser 100 to the device 10. The ends of the hollow horizontal segment 104 of the T-shaped manifold 102 slidably fit over the ends of the flexible tube 56 and the reduced portion of the mouthpiece 58.

The dispenser 100 includes a see-through, hollow cylindrical tube 106 having a cap 108 threaded thereon. The cap 108 includes an upwardly extending offset outlet tube 110 which slidably fits into the depending vertical, hollow leg 111 of the T-shaped manifold 102 and which forms with the caps 108 a circuitous passageway 112 between the interior of the hollow cylindrical tube 106 and the hollow T-shaped manifold 102.

Within the cylindrical tube 106 is a funnel 114 which is secured to the central portion thereof. As shown, the funnel 114 is adapted to hold the medicine which is to be inhalated. Extending through the funnel 114 is a capped atomizing conduit 116. Slidably fitted over the lower end of the conduit 116 below the funnel is a flexible tube 118 connected at its other end to an oxygen panel generally disposed next to a patient's bed.

Connected into the flexible tubing 118 downstream of the dispenser 100 is a hollow thumb control manifold 120, having an opening 122, which is normally open to atmosphere. To close the manifold 120, and thereby allow oxygen to be fed to the dispenser 100 one simply has to place his or her thumb over the manifold opening 122.

To use the dispenser 100 the cap 108 is removed and the funnel 114 and adjacent portion of the tube 106 are filled with medicine up to the "max fill line". The cap 108 is then threaded on to the tubing 106 and the offset tube 110 is inserted into the depending leg 111 of the T-shaped manifold 102.

The patient now can inhale the medicine by simply closing the thumb opening 122 and inhaling through the mouthpiece. This causes oxygen impinging upon the cap of the conduit 116 to flow downwardly into the medicine and then upwardly with the medicine through the passageway 112, the T manifold 102, the mouthpiece 58 and into the lungs of the user.

With the device 10 of the invention one can be assured that the patient is inhaling the atomized medicine because the proper inhalation effort will cause one or more of the flow indicators 26a–26c to rise.

To insure stabilization of the device 10 when it is being used with the medicinal dispensers 83 and 100, and as shown in FIG. 15, a platform 124 can be used. As illustrated the platform 124 has a breadth which is substantially greater than the breadth of the platform 13 of the device 10, and includes a channel 126 into which the platform 13 slidably fits.

The invention in its broader aspect is not limited to the specific described embodiments and departures may be made therefrom within the scope of the accompanying claims without departing from the principals of the invention and without sacrificing its chief advantages.

What is claimed is:

1. An incentive inhalation device for inducing respiratory exercise, comprising:
   a container having a plurality of see-through compartments therein, in each of which is a chamber,
   flow rate indicator means in each chamber which normally rests in the lower portion thereof and having a clearance between each indicator means and its chamber wall which allows free movement of the indicator means but restricts air flow thereabout to cause said indicator means to rise towards the top of its chamber when the inhalation effort by a patient reaches a precalibrated rate of air flow,
   an opening in the lower portion of each chamber connecting the chamber, to the surrounding atmosphere for lifting the flow indicator means therein,
   an opening in the top portion of each chamber,
   means associated with at least one member selected from the group consisting of said flow rate indicator means, said chambers and said openings to provide a precalibrated rate of flow for lifting said indicating means in said chambers which is different for at least two of said chambers,
   a passageway connected to each chamber through said opening in the top portion of each chamber, and
   outlet means connected to said passageway to allow a person to withdraw air from each chamber and to cause air to be drawn into each chamber through said opening therein for lifting said flow indicator means to the top of each chamber when the inhalation effort is at least the precalibrated rate of air flow for each chamber.

2. The inhalation device of claim 1, wherein the openings in the lower portion of at least two of said chambers are of different sizes to thereby provide different rates of air flow for said chambers.

3. The inhalation device of claim 1, wherein the breadths of at least two of said chambers are different to thereby provide different rates of air flow for said chambers.

4. The inhalation device of claim 1, wherein the precalibrated rate of flow is less for said first chamber than the rate for said second chamber so that the inhalation effort required to raise the flow rate indicator to the top of first said chamber is less than the inhalation effort required to raise the flow rate indicator to the top of second said chamber.

5. A self-supporting incentive inhalation device for inducing respiratory exercise, comprising:
   a container having a plurality of transparent compartments in side by side relationship along the longitudinal axis of said container,
   said compartments each having a top wall, a bottom wall, a vertical wall therebetween, and a chamber therewithin which extends from said bottom wall to said top wall,
   a light-weight article in each of said chambers which is normally in the lower portions thereof,
   a slot in each of said compartments which extends through the lower portion thereof and connects each of said chambers to the surrounding atmosphere at a point at least partially below each of said articles,
   a passageway in said container which extends over said compartment top walls and has an outlet adjacent one of the outer of said compartments,
   a restricted port in each compartment which extends through said top wall thereof and connects said chambers to said passageway,
   said article in each chamber including means adapted to close said restricted port in said respective chamber,
   a ridge in the other of the outer of said compartments dependent from the top wall thereof to prevent said article from closing said restricted port therein,
   breathing conduit means connected to said outlet to allow a person to withdraw air from said chambers through said passageway, whereupon said article in said chamber adjacent said outlet rises to the top thereof and closes said top port when a person inspires air at a precalibrated flow rate, said article in each intermediate chamber sequentially rises to the top thereof and closes each intermediate top port when a person inspires predetermined additional amounts of air at a precalibrated flow rate, and said article in the last of said chamber rises to the top thereof and contacts said depending ridge therein when a person inspires still an additional predetermined amount of air at a precalibrated flow rate, and wherein the precalibrated rate of flow for lifting said chambers is different for at least two of said chambers.

6. The inhalation device of claim 5, wherein said means includes flexible tubing and a mouthpiece connected to said tubing, and wherein said device includes bracket means along one side thereof for releasably holding said tubing and mouthpiece to said device.

7. The inhalation device of claim 5 in which a medicinal dispenser is connected to said outlet for dispensing atomized medicine upon inhalation, wherein said dispenser includes:

a container for holding medicine to be inhaled, gas conveying means adapted to be connected to a source of gas and positioned within said container for atomizing the medicine therewith, and a passageway in fluid communication with said breathing conduit means for conveying atomized medicine from said medicament container to a person upon inhalation by said person.

8. The inhalation device of claim 5 in which a medicinal dispenser is connected to said outlet for dispensing medicine upon inhalation, wherein said dispenser includes:

a container having a funnel shaped base for holding medicine to be atomized, an atomizing conduit means extending within said funnel shaped base and adapted to atomize medicine held by said funnel, flexible tubing adapted to be connected to said atomizing conduit means and to a source of oxygen for providing oxygen to said atomizing conduit means for atomization of the medicine, means operatively connected to said flexible tubing for controlling the flow of oxygen therethrough to thereby provide to said atomizing conduit means only when the medicine is to be atomized, and a circuitous passageway in fluid communication with said breathing conduit means for conveying atomized medicine from said container into said outlet upon inhalation by a person.

9. The inhalation of claim 8 in which a removable platform is removably attached to the bottom of the device when the medicinal dispenser is to be used to provide increased stability.

10. A self-supporting incentive inhalation device for inducing respiratory exercise, comprising:

a container having first, second and third see-through vertical chambers therein adjacent one another and vertical when the device is in an upright position, a ball in each chamber which normally rests in the lower portion thereof and having a clearance with its chamber walls which allows free movement of the ball but restricts air flow thereabout to cause said ball to rise towards the top of its chamber when the inhalation effort by a patient reaches a precalibrated rate of air flow, and wherein each clearance between each ball and its chamber wall is different whereby, the precalibrated rate of flow increases for each chamber, a slot in each of said chambers which extends through the lower portion thereof and connects each of said chambers to the surrounding atmosphere at a point at least partially below each of said balls, a passageway in said container which extends over said chambers and has an outlet adjacent the first of said chambers, a restricted port in each chamber which extends through the top thereof and connects said chambers to said passageway, means in said third chamber to prevent said ball therein from closing said restricted port therein, each of said restricted ports in said first and second chambers being aligned with the center of said ball in said respective chamber;

means connected to said outlet to allow a person to withdraw air from said chambers through said passageway, whereupon said ball in said chamber adjacent said rises to the top thereof and closes said top port when a person inspires air at a precalibrated flow rate, said ball in the intermediate chamber sequentially rises to the top thereof and closes said intermediate top port when a person inspires a precalibrated increased flow rate, and said ball in the last of said chambers rises to the top thereof whereupon said means therein prevents said ball from closing its top port when a person inspires a still further increased flow rate.

11. The inhalation device of claim 10, wherein said flow rate indicators are balls of different sizes so that the precalibrated rate of flow for raising said balls is different for each chamber.

12. The inhalation device of claim 11, wherein the rate in the first chamber is reduced by providing a larger ball therein which increases the lifting surface for incoming air being drawn through said lower opening.

13. The inhalation device of claim 10, wherein said ball in the first chamber is larger than the ball in said second chamber which, in turn, is larger than the ball in said third chamber, so that the precalibration rate for said first chamber is the lowest and the precalibration rate for said third chamber is the highest.

14. The inhalation device of claim 13, wherein said third ball is heavier than said first two balls to thereby provide the highest precalibration rate.

15. The inhalation device of claim 13, wherein the precalibration rate for the first chamber is about 600 cubic centimeters per second, about 900 cubic centimeters for said second chamber and about 1200 cubic centimeters for said third chamber.

* * * * *

UNITED STATES PATENT AND TRADEMARK OFFICE
CERTIFICATE OF CORRECTION

PATENT NO. : 4,114,607  Page 1 of 2
DATED : September 19, 1978
INVENTOR(S) : Ronald D. Russo It is certified that error appears in the above–identified patent and that said Letters Patent are hereby corrected as shown below:

First page, delete the drawing and insert the following:

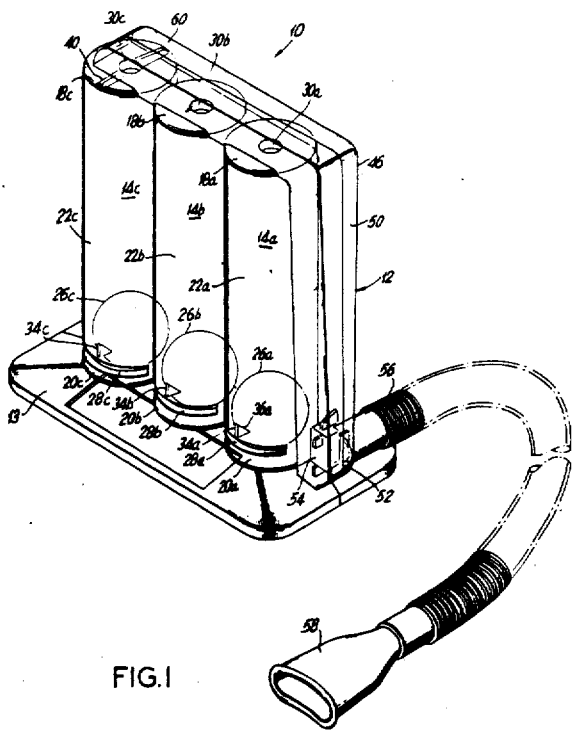

FIG.1

UNITED STATES PATENT AND TRADEMARK OFFICE
CERTIFICATE OF CORRECTION

PATENT NO. : 4,114,607
DATED : September 19, 1978
INVENTOR(S) : Ronald D. Russo

It is certified that error appears in the above-identified patent and that said Letters Patent are hereby corrected as shown below:

Col. 2, line 17, correct the spelling of "causes";

line 62, correct the spelling of "obtain".

Col. 5, line 37, correct the spelling of "chamber".

Col. 6, line 56, correct "26i a, and" to read -- 26a, --.

Col. 8, line 11, correct "26i a" to read -- 26a --;

line 21, correct "is" (first occurrence) to read -- of --.

Col. 13, line 30, correct "claim 8" to read -- claim 7 --.

Signed and Sealed this

Seventeenth Day of July 1979

[SEAL]

Attest:

LUTRELLE F. PARKER

Attesting Officer    Acting Commissioner of Patents and Trademarks